(12) United States Patent
Zhuang et al.

(10) Patent No.: US 10,667,932 B2
(45) Date of Patent: Jun. 2, 2020

(54) INTRAVASCULAR STENT

(71) Applicant: Lifetech Scientific (Shenzhen) Co., Ltd., Shenzhen (CN)

(72) Inventors: Shaochun Zhuang, Shenzhen (CN); Wenjiao Lin, Shenzhen (CN); Ge Chen, Shenzhen (CN); Kai Zhang, Shenzhen (CN); Hao Wu, Shenzhen (CN)

(73) Assignee: Biotyx Medical (Shenzhen) Co. Ltd., Shenzhen (CN)

( * ) Notice: Subject to any disclaimer, the term of this patent is extended or adjusted under 35 U.S.C. 154(b) by 169 days.

(21) Appl. No.: 15/739,038

(22) PCT Filed: Jun. 27, 2016

(86) PCT No.: PCT/CN2016/087298
§ 371 (c)(1),
(2) Date: Dec. 21, 2017

(87) PCT Pub. No.: WO2017/005107
PCT Pub. Date: Jan. 12, 2017

(65) Prior Publication Data
US 2018/0185182 A1    Jul. 5, 2018

(30) Foreign Application Priority Data

Jul. 7, 2015  (CN) .......................... 2015 1 0395101

(51) Int. Cl.
*A61F 2/915*    (2013.01)
*A61L 31/02*    (2006.01)
(Continued)

(52) U.S. Cl.
CPC ............ *A61F 2/915* (2013.01); *A61L 31/022* (2013.01); *A61L 31/06* (2013.01); *A61L 31/18* (2013.01);
(Continued)

(58) Field of Classification Search
CPC .............................................. A61F 2250/0098
See application file for complete search history.

(56) References Cited

U.S. PATENT DOCUMENTS

| | | | |
|---|---|---|---|
| 6,758,859 B1 | 7/2004 | Dang et al. | |
| 2009/0198315 A1* | 8/2009 | Boudjemline | ........ A61F 2/2418 623/1.2 |

(Continued)

*Primary Examiner* — Jacqueline Woznicki
(74) *Attorney, Agent, or Firm* — Raymond Sun

(57) ABSTRACT

An intravascular stent (100, 200, 300) comprises a framework with openings and at least one radiopaque structure (103, 201, 301). Each radiopaque structure (103, 201, 301) comprises fixed bodies and radiopaque markers (105, 208, 307) filled in the fixed bodies. The fixed bodies are connected with the framework, and are at least partially disposed in the openings. The envelope enclosed area of all the radiopaque markers (105, 208, 307) in each radiopaque structure (103, 201, 301) is less than or equal to 2 mm$^2$, and a sum of effective areas of all the radiopaque markers (105, 208, 307) in each radiopaque structure (103, 201, 301) is greater than or equal to 0.15 mm$^2$, and a ratio of said sum of effective areas to said envelope enclosed area is greater than or equal to 1:5. The radiopaque structure (103, 201, 301) has a desirable visibility, and does not substantially affect the crimped diameter of the intravascular stent (100, 200, 300).

9 Claims, 2 Drawing Sheets

(51) Int. Cl.
*A61L 31/06* (2006.01)
*A61L 31/18* (2006.01)
*A61F 2/958* (2013.01)

(52) U.S. Cl.
CPC ..... *A61F 2/958* (2013.01); *A61F 2002/91575* (2013.01); *A61F 2230/0006* (2013.01); *A61F 2230/0008* (2013.01); *A61F 2230/0023* (2013.01); *A61F 2230/0045* (2013.01); *A61F 2240/001* (2013.01); *A61F 2250/0098* (2013.01)

(56) References Cited

U.S. PATENT DOCUMENTS

2012/0095546 A1* 4/2012 Yokoi .................. A61F 2/86
                                                        623/1.34
2018/0185182 A1* 7/2018 Zhuang ................ A61F 2/915
2018/0333219 A1* 11/2018 Lin ...................... A61L 29/18

* cited by examiner

INTRAVASCULAR STENT

TECHNICAL FIELD

The present disclosure relates to implantable medical devices, and in particular, to an intravascular stent having a radiopaque structure.

BACKGROUND ART

Coronary atherosclerotic heart disease, which is often referred to as a "coronary heart disease", is a kind of heart disease caused by myocardial ischemia, anoxia or necrosis due to vascular stenosis or obstruction resulting from coronary artery atherosclerotic pathological changes. Cardiac stents are widely used as implants for the treatment of such cardiovascular diseases. Generally, a cardiac stent is delivered to the diseased area through a delivery system, and then the stent is expanded to reconstruct the blood vessels to treat the "coronary heart diseases" effectively.

The existing stents for treating coronary heart diseases are mainly divided into the following two categories: non-absorbable stents and absorbable stents. The framework of the conventional non-absorbable stents is usually made of stainless steel, nickel-titanium alloy or cobalt-chromium alloy. After being implanted into the body, the visibility of a metal-based stent is primarily dependent on the framework material and the stent thickness, and the stent thickness refers to the wall thickness of the tubular structure of the stent. If the thickness of a metal-based stent is greater than 80 μm, its image can be displayed clearly on the medical imaging equipment and digital subtraction angiography (DSA) equipment, so that the position and configuration of the stent can be easily identified, providing high visibility. For a metal-based stent, the smaller the stent thickness, the better the stent is apposed to the vascular wall, as such the strut would have less shear disturbance on the blood flow inside the blood vessel, which is more helpful for preventing thrombosis formation. Accordingly, a metal-based stent with a relatively thin thickness is preferred in medical practice. However, when the thickness of a metal-based stent is less than 80 μm, its image displayed on the DSA equipment may be unclear, so that the position and configuration of the stent is not easy to identify, leading to the need for improvements in visibility.

Absorbable stents are generally made of an absorbable metal (such as magnesium and iron) and polymer (such as polylactic acid, polycaprolactone or a copolymer thereof). As the polymer material itself has a very small density and relatively low visibility, an intravascular stent that is made of the polymer with wall thickness from 120 μm to 180 μm, i.e., a polymer stent, is almost invisible with the aid of medical imaging equipment and digital subtraction angiography equipment, so that physicians are unable to accurately locate the stent during surgical operations. Therefore, the polymer stent requires an additional radiopaque structure which can be identified by physicians under DSA. By identifying the position of the radiopaque structure, a physician can determine the position or configuration of the entire stent. Namely, the problem of the low visibility of the stent framework can be addressed by using a radiopaque structure with high visibility. Therefore, the visibility of the entire stent can be improved.

For a metal-based absorbable stent, the smaller the stent thickness, the better the stent is apposed to the vascular wall, and the less the shear disturbance of the stent strut on the blood flow inside the blood vessel, which is more helpful for preventing thrombosis formation, and is helpful for shortening the period of time needed for the stent to be completely absorbed by the body. Therefore, with the development of technology, the framework of a metal-based absorbable stent becomes thinner and thinner. When the stent wall thickness is reduced to a certain extent, the visibility of the stent framework deteriorates, leading to the need for disposing a radiopaque structure to improve the entire visibility of the stent.

To address the shortcoming of low visibility of the absorbable stent framework, as disclosed in the prior art, the stent is wound with a wire made of a highly-radiopaque material at one end, alternatively, the stent framework is partially made of a highly-radiopaque material, or the framework is coated with a highly-radiopaque material, to form a radiopaque structure for improving the entire visibility of the stent. Typically, the highly-radiopaque material refers to a metal having a relatively high density, for example, a noble metal. In the prior art, in order to enable the radiopaque structure to have sufficient visibility, the coating thickness or wire diameter needs to be increased, which significantly increases the thickness of the stent, leading to the risk of thrombosis in the relatively thick stents, and increases the crimped diameter of the stent.

The crimped diameter is one of the important parameters characterizing the mechanical property of a stent, which refers to the maximum outer diameter of the stent that is compressed mechanically onto a balloon. After the stent is preloaded on the balloon, the crimped diameter determines the ability of the stent to pass through a stenosis blood vessel of a diseased area. The smaller the crimped diameter, the narrower the blood vessel that the stent can pass through. The value of the crimped diameter also affects the flare effect of the stent, that is, the greater the crimped diameter, the higher the possibility that the proximal and distal ends of the stent may be circumferentially separated from the balloon, and the higher the possibility that the stent may scratch the vascular wall, or deform or peel off from the balloon, when passing through the tortuous site.

Also as disclosed in the prior art, a hole is disposed on the polymer stent framework, and a highly-radiopaque material is pressed into the hole to form a radiopaque structure by means of gluing or welding. Such polymer stents are typically thick, with the thickness being 120 μm or more. Therefore, a relative small area of the radiopaque structure could make a clear image on the DAS equipment, and lead to high visibility accordingly. However, this method of improving the visibility of polymer stents is unsuitable for relatively thin absorbable stents, i.e., stents having the thickness less than 120 μm. This is because when the stent wall is relatively thin, the depth of the hole is small, and the thickness of the radiopaque material compressed in the hole is smaller. In the case that the area of the radiopaque structure is small, if the thickness of the radiopaque structure is relatively small, the image formed under the DSA equipment is unclear and hard to be identified. In addition, in the case that the stent thickness is constant, if the area of the radiopaque structure described above is increased only by increasing the area of the hole on the stent framework, the space of the stent framework occupied by the radiopaque structure may be increased, which may affect the deformation of the stent when the stent is crimped, thereby affecting the crimped diameter of the stent. Therefore, a suitable radiopaque structure should be disposed on an absorbable stent with thickness less than 120 μm to meet the visibility requirements, while not having a substantial affect on the crimped diameter of the stent.

SUMMARY OF THE DISCLOSURE

Accordingly, it is necessary to provide an intravascular stent having a radiopaque structure that has better visibility and less impact on the crimped diameter in regard to the above problems.

In one technical solution of the present disclosure, an intravascular stent comprises a framework having openings and at least one radiopaque structure connected with the framework. The framework is suitable for metal-based stents having a wall thickness of less than 80 μm or polymer stents having a wall thickness of less than 120 him. The metal-based stent may be a stainless steel, nickel-titanium alloy, cobalt-chromium alloy, iron-based, magnesium-based or zinc-based bare metal stent, or may be a metal-based polymer-eluting stent described above.

Each radiopaque structure comprises fixed bodies and radiopaque markers filled within the fixed bodies. The fixed bodies are connected with the framework, and at least partially disposed in the openings. For example, the radiopaque structure comprises a plurality of fixed bodies. At least one of the fixed bodies is disposed on the framework, while the other fixed bodies are disposed in the openings, with connection to the framework through additional connectors. That is, a part of the radiopaque markers may be located on the framework and the other radiopaque markers may be located in the openings. Alternatively, the plurality of fixed bodies are all disposed in the openings and connected with the framework directly. That is, the radiopaque markers are all located in the openings. Alternatively, the plurality of fixed bodies is all disposed in the openings, with connection to the framework through additional connectors. That is, the radiopaque markers are all located in the openings.

The fixed body may be provided with holes, for example a through-hole or groove. All the holes are filled with radiopaque markers, alternatively, a part of holes are filled with radiopaque markers. The radiopaque marker in the hole may protrude from the fixed body, or may be flush with the fixed body, or may be depressed in the thickness direction of the fixed body. The radiopaque marker may be heavy metal, for example, at least from one of gold, platinum, osmium, rhenium, tungsten, iridium, rhodium or tantalum. Alternatively, the radiopaque marker may be a mixture of the heavy metal described above and polymer, where the mass fraction of the heavy metal is greater than or equal to 70%. As an example, the polymer may be a degradable polymer selected from PLLA, PLGA, PAGA, PGLA or PLA.

As an embodiment of the present disclosure, each radiopaque structure may satisfy the following conditions: the envelope enclosed area of all the radiopaque markers in each radiopaque structure may be less than or equal to 2 mm², a sum of effective areas of all the radiopaque markers may be greater than or equal to 0.15 mm², and a ratio of the sum of effective areas to the envelope enclosed area may be greater than or equal to 1:5. Wherein, the envelope enclosed area may be less than or equal to 1.5 mm². Further, the envelope enclosed area may be less than or equal to 0.7 mm². The envelope described above refers to a closed curve that is formed by meeting the most prominent points on the edge of all the radiopaque markers filled in the fixed body of each radiopaque structure in an internally tangent manner by using a smooth transition curve. The effective radiopaque area refers to a sum of the areas of all the radiopaque markers filled in the fixed bodies.

As another embodiment of the present disclosure, a sum of the effective areas may be greater than or equal to 0.19 mm². Further, a sum of the effective areas may be greater than or equal to 0.22 mm².

As yet another embodiment of the present disclosure, a ratio of the sum of the effective areas to the envelope enclosed area may be greater than or equal to 1:4. Further, a ratio of the sum of the effective areas to the envelope enclosed area may be greater than or equal to 1:3.2.

As an embodiment of the present disclosure, the area of the radiopaque markers in each fixed body may be less than 0.1 mm².

The included angle between the major diameter of the envelope and the axial direction of the framework may be less than 45 degrees, or the included angle between the major diameter of the envelope and the axial direction of the framework is less than that between the major diameter and the circumferential direction of the framework.

In an intravascular stent described above, each radiopaque structure may comprise at least three fixed bodies, wherein at least two fixed bodies are disposed in the openings, and the central connection line of the radiopaque markers in the two fixed bodies is parallel to the axial direction of the framework.

The present disclosure provides an intravascular stent, of which the visibility is improved with the precondition that the overall crimped diameter remains unchanged, by setting parameters for the proper effective radiopaque area, the envelope enclosed area, the ratio therebetween, and by setting proper positions of the radiopaque markers.

DETAILED DESCRIPTION OF THE EMBODIMENTS

Figure 1:
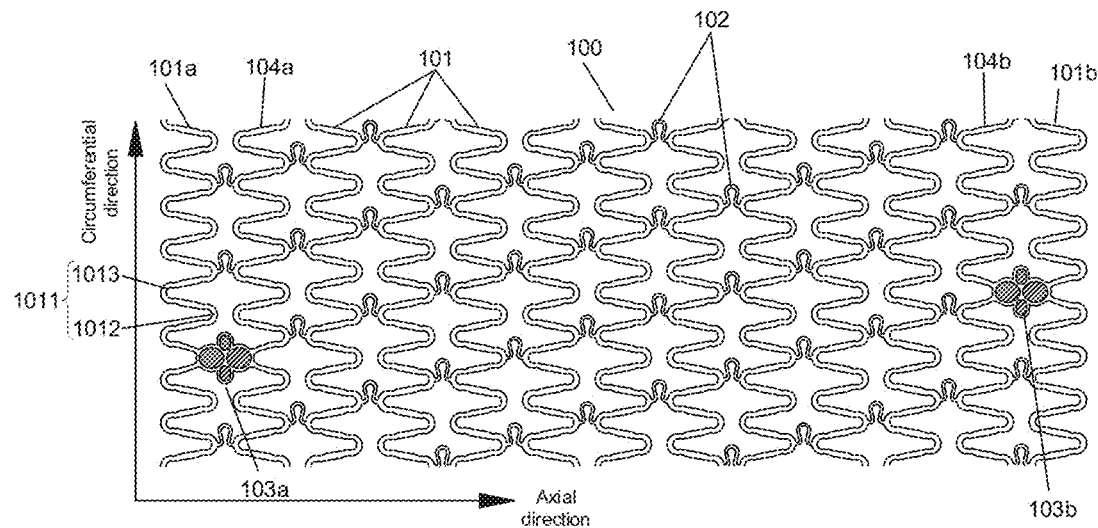
FIG. 1 illustrates an axially unfolded view of an intravascular stent according to embodiment 1 of the present disclosure.

To help understand the present disclosure, the disclosure will be further explained comprehensively by referring to the accompanying drawings. In the drawings, the preferred embodiments of the present disclosure are provided. However, the present disclosure may be embodied in many different ways and not limited to the embodiments described herein. Rather, the purpose of providing these embodiments is to make the disclosure of the present disclosure more thorough and complete.

Unless defined otherwise, all technical and scientific terms used herein generally have the same meaning as commonly understood by technicians in the field. The terms used in the description herein are only intended to illustrate the purposes of the embodiments, but not to limit the scope of the present disclosure in any way.

The term "connected" used herein may refer to a direct connection of a component A with a component B, or an inter-connection of a component A and a component B via an another component C.

The present disclosure makes improvements to the radiopaque structure of metal-based stents with wall thickness less than 80 μm or polymer stents with wall thickness less than 120 μm, considering the fact that the visibility of said stents should be improved by increasing the effective radiopaque area of the radiopaque structure, with the precondition of assuring that the increased effective radiopaque area does not have a large impact on the crimped diameter of the stent.

Specifically, the present disclosure relates to an intravascular stent that comprises at least one radiopaque structure, which is connected to a stent framework with openings. Each radiopaque structure comprises fixed bodies with holes and radiopaque markers filled within. The fixed bodies may have at least one hole disposed on the framework. That is, a part of the radiopaque markers may be located on the framework, while the other part of the fixed bodies may be located in the openings and connected with the framework through additional connectors. Alternatively, the fixed bodies are all disposed in the openings and directly connected with the framework. That is, the radiopaque markers are all disposed in the openings. Alternative y, the fixed bodies are all disposed in the openings and connected with the framework through additional connectors. That is, the radiopaque markers are all located in the openings.

The shape of said radiopaque markers is circle, ellipse, triangle, polygon, or other irregular geometrical shape. The filling processes of radiopaque markers include tamping, hot-pressing, press-riveting, welding, sintering, plating or coating, etc.

The present disclosure relates to an intravascular stent, of which the effective radiopaque area, the envelope enclosed area and the ratio therebetween are key parameters for determining the visibility of the radiopaque structure. The effective radiopaque area refers to a sum of the area of the radiopaque markers filled in the fixed bodies. The envelope refers to a closed curve that is formed by meeting the most prominent points on the edge of all the radiopaque markers filled in the fixed body of each radiopaque structure in an internally tangent manner by using a smooth transition curve.

In the case that the wall thickness of the intravascular stent is fixed, the total amount of the radiopaque markers in each radiopaque structure is determined by the effective radiopaque area. The total area occupied by the radiopaque markers distributed in the holes is characterized by the enclosed area of the envelope. The degree of density of the radiopaque markers within the envelope is characterized by the ratio of the effective area to the envelope enclosed area. In the case that the thickness is fixed, the visibility of the radiopaque structures is influenced by the effective radiopaque area, the envelope enclosed area and the ratio of the effective radiopaque area to the envelope enclosed area. Wherein, the radiopaque structure has the visibility only when the effective radiopaque area is greater than a certain value. With sufficient effective radiopaque area, the larger the envelope enclosed area, the larger the radiopaque area produced by the radiopaque structure under the DSA equipment, which is helpful for visual identification. However, the larger the envelope enclosed area means the larger the distribution of radiopaque markers on the stent framework, which means the higher possibility of affecting the mechanical property of the stent. Therefore, the enclosed area of the envelope should be limited to a certain range. The larger the ratio of the effective radiopaque area to the envelope enclosed area, the denser the distribution of the radiopaque markers. If the ratio is equal to 1:1, all the radiopaque markers in each radiopaque structure are gathered to a whole body, which means the radiopaque markers are inter-connected without a gap. The smaller the ratio of the effective radiopaque area to the envelope enclosed area, the more sparse the distribution of all the radiopaque markers in each radiopaque structure. If the distribution of all the radiopaque markers in each radiopaque structure is too sparse, which means the gaps among the radiopaque markers are too large, the radiopaque markers cannot interconnect to realize a radiopaque structure with good visibility, and each radiopaque marker cannot realize a clear marker for visual identification as well. Namely, in order to ensure a high visibility of each radiopaque structure, the effective radiopaque area, the envelope enclosed area and the ratio therebetween of all the radiopaque markers in each radiopaque structure should be limited to an appropriate range.

In the present disclosure, the envelope enclosed area of all radiopaque markers in each radiopaque structure may be less than or equal to 2 $mm^2$, a sum of effective areas of all the radiopaque markers may be greater than or equal to 0.15 $mm^2$, and a ratio of the sum of effective areas to the envelope enclosed area may be greater than or equal to 1:5. Further, a sum of the effective areas may be greater than or equal to 0.19 $mm^2$. Moreover, a sum of the effective areas may be greater than or equal to 0.22 $mm^2$. A ratio of the sum of effective areas to the envelope enclosed area may be greater than or equal to 1:4. Further, a ratio of the sum of effective areas to the envelope enclosed area may be greater than or equal to 1:3.2. The area of the radiopaque marker in each fixed body may be less than 0.1 $mm^2$.

It is noted that the thickness of the radiopaque marker may be slightly greater or smaller than the thickness of the fixed body, or may be the same as the thickness of the fixed body, that is, being flush with the fixed body. If the thickness of the radiopaque marker is greater than the thickness of the fixed body, the visibility is improved. If the thickness of the radiopaque marker is smaller than the thickness of the fixed body, the visibility is weakened. Also, the boundary of the radiopaque marker may coincide with the boundary of the hole in the fixed body, or alternatively not coincide. If the radiopaque marker protrudes slightly from the boundary of the hole in the fixed body, the effective radiopaque area of the radiopaque marker does not contain the radiopaque marker outside the boundary of the hole. If the hole of the fixed body is not fully filled with the radiopaque marker, which means there is a gap between the radiopaque marker and the fixed body, the effective radiopaque area of the radiopaque marker does not contain the gap.

Also, the effective radiopaque area refers to an area of a visible pattern that is formed by the radiopaque markers under DSA, of which can be observed by naked eyes. That is, a visible pattern formed by all the radiopaque markers. If an intravascular stent still comprises an ineffective radiopaque marker that does not contribute to the visibility, for example, with the long distance apart, the ineffective radiopaque marker fails to combine with an effective radiopaque marker to enhance the visibility, the ineffective radiopaque marker is not construed to be the effective radiopaque marker described herein. The ineffective radiopaque marker is not included in the radiopaque structure of the present disclosure. Correspondingly, the ineffective radiopaque marker is excluded from the envelope defined herein. That is, the envelope of the present disclosure is not the closed curve that is formed by meeting the most prominent points on the edge of the effective radiopaque markers as well as the most prominent points on the edge of the effective radiopaque markers in an internally tangent manner by using a smooth transition curve. With the value of the effective radiopaque area, the envelope enclosed area and the ratio therebetween, being satisfied, as disclosed above, there are multiple solutions on how to set the position and size relationships among various separated radiopaque markers. The technical solution of the present disclosure will be further described below by referring to the particular embodiments.

Embodiment 1

Please refer to FIG. 1, which illustrates a structural schematic view of an unfolded intravascular stent 100 along the axial direction. The intravascular stent 100 is a thin-wall iron-based tubular structure having a thickness of 50 μm, and having axial and circumferential directions. In practice, the axial direction of the stent is provided substantially along the axial direction of a blood vessel.

Figure 2:
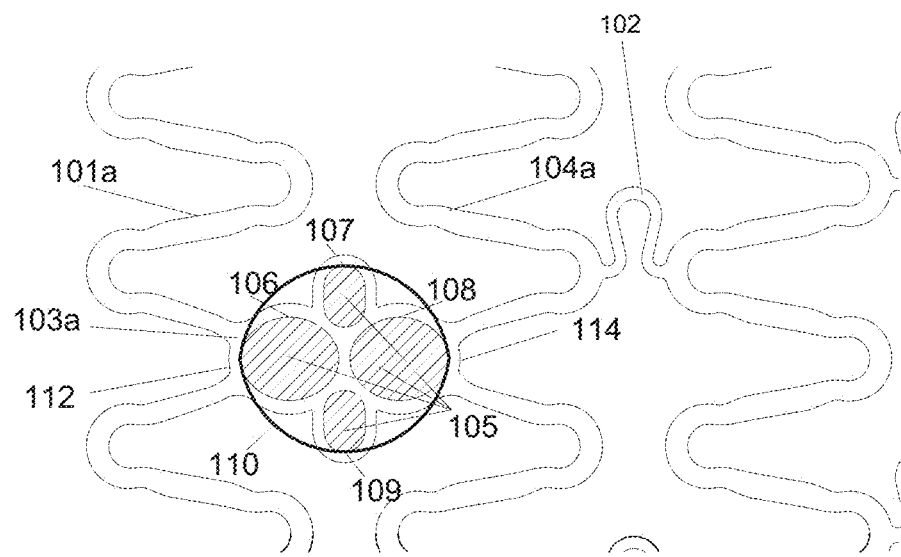
FIG. 2 illustrates a partially enlarged structural view of a radiopaque structure of an intravascular stent according to embodiment 1 of the present disclosure.

Please refer to both FIG. 1 and FIG. 2. The intravascular stent 100 comprises a plurality of separated wave-shaped rings 101. Each wave-shaped ring 101 comprises a plurality of O-shaped sine wave unit 1011 which are connected end to end. Each sine wave unit comprises peaks 1012 and valleys 1013. The looping direction of each wave-shaped ring 101 is the circumferential direction of the stent 100. Any two adjacent wave-shaped rings 101 are connected through a connecting rod 102. Among any two adjacent wave-shaped rings 101, all the peaks of one wave-shaped ring 101 are axially aligned with all the valleys of the other wave-shaped ring 101. The connecting rod 102 between two adjacent wave-shaped rings 101 is connected with the peaks of one wave-shaped ring 101 and the valleys of the other wave-shaped ring 101. The plurality of wave-shaped rings 101 and the connecting rods 102 constitute a framework of the intravascular stent 100, and the gaps between all the wave-shaped rings 101 constitute the openings, with the connecting rods 102 being excluded.

The plurality of wave-shaped rings 101 includes a proximal ring 101a and a distal ring 101b, which are located at the axial ends of the intravascular stent 100 respectively. The first wave-shaped ring 104a is adjacent to the proximal ring 101a, and the second wave-shaped ring 104b is adjacent to the distal ring 101b. The proximal radiopaque structure 103a is connected with the proximal ring 101a and the first wave-shaped ring 104a. The distal radiopaque structure 103b is connected with the distal ring 101b and the second wave-shaped ring 104b. Namely, in this embodiment, both the proximal radiopaque structure 103a and the distal radiopaque structure 103b are located in the openings, and directly connected with the framework. The proximal radiopaque structure 103a and the distal radiopaque structure 103b have the same shape and dimension. To take the proximal radiopaque structure 103a, for example in following paragraph, the radiopaque structure of the intravascular stent of the present disclosure will be described.

FIG. 2 is an enlarged view of the intravascular stent 100 of FIG. 1, which comprises the proximal radiopaque structure 103a. As shown in FIG. 2, the proximal radiopaque structure 103a comprises four ring-shaped and interconnected fixed bodies, and the radiopaque markers 105 that are filled in the hole of each fixed body. In this embodiment, the material of the radiopaque markers 105 is gold. The holes include a first fixing hole 106, a second fixing hole 107, a third fixing hole 108 and a fourth fixing hole 109, which are all elliptic.

The four holes have different inside diameters. Among them, the first fixing hole 106 and the third fixing hole 108 have the same inside diameter. The central connection line of the first fixing hole 106 and the third fixing hole 108 is parallel to the axial center line of the intravascular stent 100, that is, the central connection line of the radiopaque markers in these two fixing holes is parallel to the axial center line of the framework. The second fixing hole 107 and the fourth fixing hole 109 have the same inside diameter. The central connection line of the second fixing hole 107 and the fourth fixing hole 109 is along the circumferential direction of the intravascular stent 100. The first fixing hole 106, the second fixing hole 107, the third fixing hole 108 and the fourth fixing hole 109 are connected end to end, and located in the gap between the proximal ring 101a and the first wave-shaped ring 104a.

The first fixing hole 106 is directly connected with the peaks of the proximal ring 101a, and located on the side of one peak 112 of the proximal ring 101a, facing the first wave-shaped ring 104a. The third fixing hole 108 is directly connected with the valleys of the first wave-shaped ring 104a, and located on the side of the first wave-shaped ring 104a, facing the first peak 114 of the proximal ring 101a. The second fixing hole 107 is connected with the proximal ring 101a and the first wave-shaped ring 104a through the first fixing hole 106 and the third fixing hole 108 respectively. Similarly, the fourth fixing hole 109 is connected with the proximal ring 101a and the first wave-shaped ring 104a through the first fixing hole 106 and the third fixing hole 108 respectively. Namely, each fixing hole is connected with two adjacent fixing holes in a way of sharing a part of the boundary to cluster as a whole body. The second fixing hole 107 and the fourth fixing hole 109 have a relatively smaller area, and are showed in ellipse, with the major diameter direction being along the circumferential direction of the stent and the minor diameter direction being along the axial direction of the stent. The second fixing hole 107 and the fourth fixing hole 109 are disposed between the proximal ring 101a and the first wave-shaped ring 104a. The four fixing holes described above are filled with the radiopaque markers 105, with the edge of the radiopaque markers 105 coinciding with the edge of each fixing hole. The thickness of the radiopaque markers 105 matches with the depth of each fixing hole, that is, the thickness of the radiopaque markers 105 is 50 μm.

In the structural view showing the dimension and shape with the intravascular stent unfolded axially, that is, in the axial unfolding view of the stent that is not expanded by a balloon, the most prominent points on the edges of the radiopaque markers 105 filled in the first fixed body 106, the second fixed body 107, the third fixed body 108 and the fourth fixed body 109 are connected sequentially by a curve, to form an approximately elliptic envelope 110. The major diameter of the envelope 110 is provided along the axial direction of the intravascular stent 100, and the minor diameter is provided along the circumferential direction of the intravascular stent 100. The enclosed area of the envelope 110 is 0.3863 mm$^2$, the effective development area of the radiopaque structure 103, that is, the sum of areas of the radiopaque markers 105 in the first fixing hole 106, the second fixing hole 107, the third fixing hole 108 and the fourth fixing hole 109, is 0.2238 mm$^2$, and the ratio of the effective radiopaque area to the enclosed area of the envelope 110 is 1:1.73.

When the intravascular stent 100 is crimped, the proximal ring 101a and the first wave-shaped ring 104a that is connected with the proximal ring 101a deform circumferentially, the second fixing hole 107 and the fourth fixing hole 109 can enter the gap between the proximal ring 101a and the first wave-shaped ring 104a that is adjacent to the proximal ring, without limiting the proximal ring 101a and the first wave-shaped ring 104a, thereby not substantially affecting the crimped diameter of the stent. Based on the comparison test of the stent of this embodiment and a stent that has the same framework structure without a radiopaque structure, the crimped diameters are both 0.98 mm.

Figure 3:
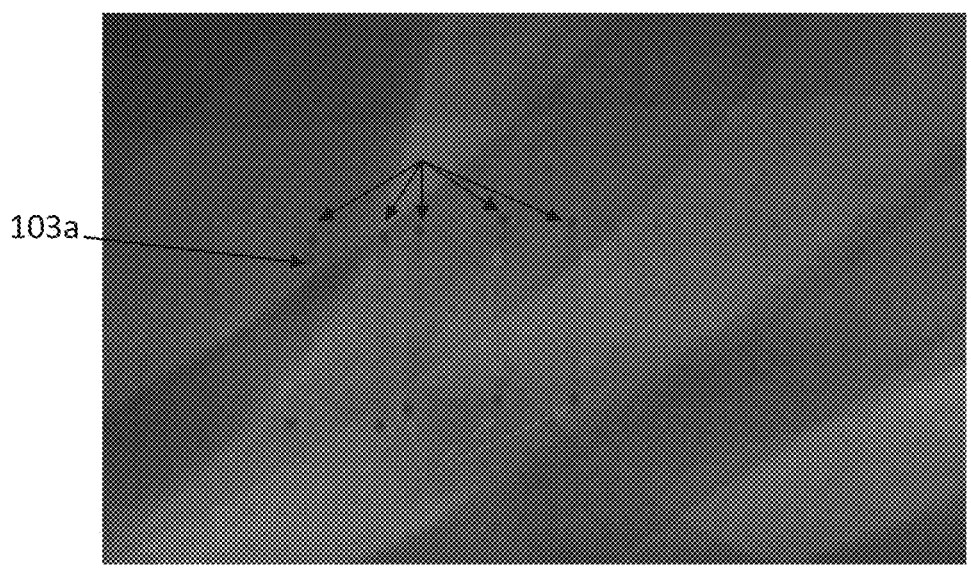
FIG. 3 illustrates DSA images of intravascular stents according to embodiments 1-3 of the present disclosure.

FIG. 3 shows an image of the stent of FIG. 1, which is crimped on the surface of a balloon, with a part of the proximal radiopaque structure 103a being placed under a DSA equipment together with the balloon. In FIG. 3, the topmost row of black spots and the bottommost row of black spots are formed by the images of development rings of a balloon delivery system, and the image of the radiopaque structure 103a is located near to the first balloon development ring from the left in the topmost row and slightly lower than the position of the balloon development ring. It can be seen that although the radiopaque structure 103a comprises four separate radiopaque markers, the four radiopaque markers gather together and match with one another, visually representing an entire pattern with a desirable visibility.

In this embodiment, the design of distributing the radiopaque markers 105 in the four fixing holes is advantageous to fix each radiopaque marker due to large thickness-to-width ratio of the radiopaque marker when filling the radiopaque marker in each fixing hole. Taking the radiopaque marker filled in the first fixing hole 106 in this embodiment as an instance, its thickness is equivalent to the stent thickness, being 50 μm, and its maximum width is equivalent to the maximum width of the first fixing hole 106. The fixing hole 106 is elliptic, with the major diameter being 360 μm. As a result, the radiopaque marker can be firmly secured into the first fixing hole 106 with the thickness-to-width ratio being 50:360.

Also, the positional relationship of the four fixed bodies, i.e., the positional relationship of the four radiopaque markers, can be appropriately arranged and optimized, so that the fixed design of radiopaque structure would have minimal impact on the structure of stent framework, and would have no influence on the crimped diameter of the stent accordingly.

Embodiment 2

Figure 4:
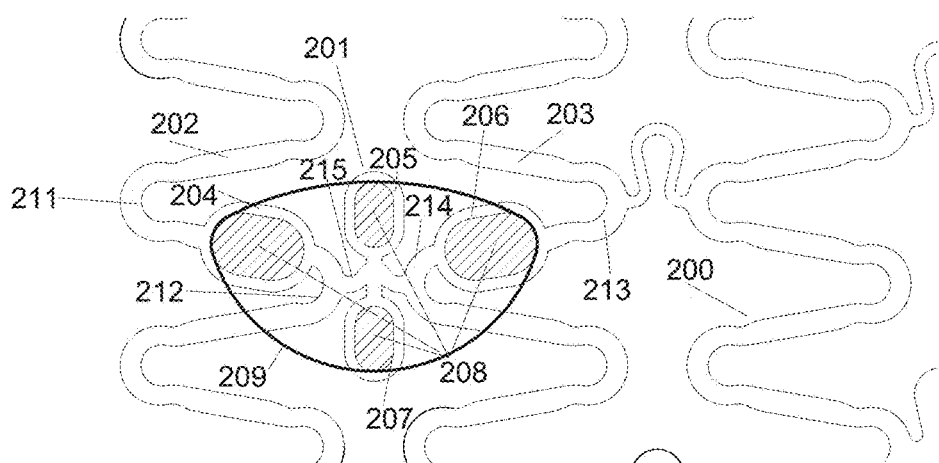
FIG. 4 illustrates a structural view of a radiopaque structure according to embodiment 2 of the present disclosure.

FIG. 4 is a partially enlarged view of an intravascular stent 200 of this embodiment. Compared to embodiment 1, the framework of intravascular stent 200 of this embodiment has the same structure, while the difference from embodiment 1 is that the thickness of the intravascular stent 200 in this embodiment is 60 μm.

The radiopaque structure 201 in this embodiment comprises four fixed bodies with through-holes. The through-holes include a first fixing hole 204, a second fixing hole 205, a third fixing hole 206 and a fourth fixing hole 207, all of which are elliptic. The radiopaque markers 208 are a mixture of heavy metal platinum powder and PLLA, with the mass fraction of platinum powder being 90%. The radiopaque markers 208 are filled within each said fixing holes, and the area of radiopaque markers in each fixing hole is less than 0.1 mm².

The four holes have different inside diameters. Among them, the first fixing hole 204 and the third fixing hole 206 have the same inside diameter. The central connection line of the first fixing hole 204 and the third fixing hole 206 is provided along the axial direction of the intravascular stent 200, that is, the central connection line of the radiopaque markers in these two fixing holes is parallel to the axial center line of the intravascular stent 200. The second fixing hole 205 and the fourth fixing hole 207 have the same inside diameter which is smaller than the inside diameter of the first fixing hole 204 and the third fixing hole 206, and the central connection line of the second fixing hole 205 and the fourth fixing hole 207 is provided along the circumferential direction of the intravascular stent 200.

The fixed body with the first fixing hole 204 is disposed on a proximal ring 202 and is a part of the proximal ring 202. The fixed body with the third fixing hole 206 is disposed on a first wave-shaped ring 203 and is a part of the first wave-shaped ring 203, wherein a valley 211 of the proximal ring 202 is axially aligned with a peak 203 of the first wave-shaped ring 203, and, a peak 212 of the proximal ring 202 is axially aligned with a valley 214 of the first wave-shaped ring 203.

The second fixing hole 205 and the fourth fixing hole 207 are located in the gap between the proximal ring 202 and the first wave-shaped ring 203. The second fixing hole 205 and the fourth fixing hole 207 are connected through a connector 215. Namely, a part of the fixed body is located on the framework, and the other parts are located in the openings.

The connector 215 comprises two branches located in the axial direction and two branches located in the circumferential direction. The two branches in the axial direction of the connector 215 are respectively connected with the peak 212 of the proximal ring 202 and the valley 214 of the first wave-shaped ring 203, and the two branches in the circumferential direction of the connector 215 are respectively connected with the second fixing hole 205 and the fourth fixing hole 207.

In the structural view showing the dimension and shape of the intravascular stent unfolded axially, the most prominent points on the edges of the radiopaque markers 204 filled in the first fixed body 205, the second fixed body 206, the third fixed body 108 and the fourth fixed body 207 are connected sequentially by using a curve, to form an approximately tapered bowl-shaped envelope 209. The major diameter of the envelope 209 is provided along the axial direction of the intravascular stent 200, and the minor diameter is provided along the circumferential direction of the intravascular stent 200. The major diameter of the envelope 209 is 1.26 mm, and the minor diameter thereof is 0.73 mm. In this embodiment, the enclosed area of the envelope 209 is 0.6897 mm², and the effective radiopaque area of the radiopaque structure 201 is 0.2134 mm², and the ratio of the effective radiopaque area to the envelope enclosed area is 1:3.23.

As compared to embodiment 1, the effective area of the radiopaque markers in this embodiment is approximate, but the enclosed area of the envelope 209 is larger, and the ratio of the effective radiopaque area to the envelope enclosed area is smaller, indicating that the distribution of the radiopaque markers is sparser. When the intravascular stent 200 is crimped, the proximal ring 202 and the first wave-shaped ring 203 connected therewith deform circumferentially. Since the second fixing hole 205 and the fourth fixing ho e 207 of the radiopaque structure 201 can enter the gap between the proximal ring 202 and its adjacent first wave-shaped ring 203, the proximal ring 202 and the first wave-shaped ring 203 will not be confined. Therefore, the impact of the radiopaque structure 103a on the wave-shaped ring during crimping is reduced. While as the first fixing hole 204 and the third fixing hole 206 are respectively located on the proximal ring 202 and the first wave-shaped ring 203 of the intravascular stent 200, during the inflation process, the deformation of the intravascular stent 200 may result in the change in position of the first fixing hole 204 and the third fixing hole 206, thereby not substantially affecting the crimped diameter of the stent. Based on the comparison test of the stent of this embodiment and a stent that has the same framework structure without a radiopaque structure, the crimped diameter of the stent without a radiopaque structure is 0.99 mm, and the crimped diameter of the stent in this embodiment is 1.00 mm, indicating no significant difference therebetween.

FIG. 3 shows an image of the stent having the radiopaque structure of this embodiment under a DSA equipment. In the figure, the second stent from the right is the intravascular stent 200, it can be seen that the radiopaque structure 201 has a desirable visibility.

Embodiment 3

Figure 5:
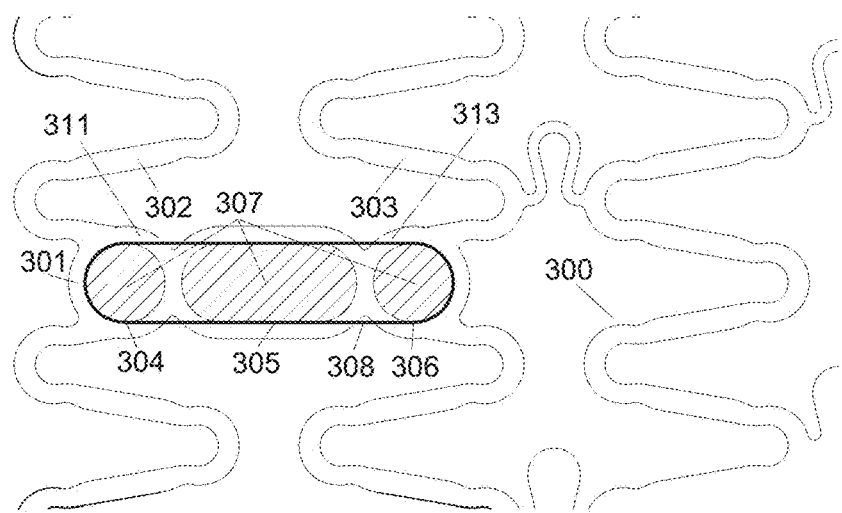
FIG. 5 illustrates a structural view of a radiopaque structure according to embodiment 3 of the present disclosure.

FIG. 5 illustrates a partially enlarged structural view of the intravascular stent 300 provided for this embodiment. The thickness of the intravascular stent 300 of this embodiment is 70 μm.

In the figure, a radiopaque structure 301 is located at the proximal end of the intravascular stent 300, connected with a proximal ring 302 and a first wave-shaped ring 303; that is, the radiopaque structure 301 is entirely located in the openings and directly connected with the framework. The radiopaque structure 301 comprises three fixed bodies with holes and radiopaque markers 307 filled within. In this embodiment, the radiopaque marker 307 is tantalum. The holes include a first fixing hole 304 and a third fixing hole 306, which are round, and a second fixing hole 305, which is elliptic.

The first fixing hole 304 and the third fixing hole 306 have the same inside diameter. The central connection line of the first fixing hole 304, the second fixing hole 305 and the third fixing hole 306 is provided along the axial direction of the intravascular stent 300.

The fixed body with the first fixing hole 304 is directly connected with the proximal ring 302, and located on the side of one peak 311 of the proximal ring 302 departing from the first wave-shaped ring 303. The fixed body with the third fixing hole 306 is directly connected with the first wave-shaped ring 303, and located on the side of one valley 313 of the first wave-shaped ring 303 departing from the proximal ring 302. The second fixing hole 305 is located in the gap between the proximal ring 302 and the first wave-shaped ring 303, and directly connected with the peak 311 of the proximal ring 302 and the valley 313 of the first wave-shaped ring 303, in which the peak 311 is aligned with the valley 313 along the axial direction of the stent.

In this embodiment, on the intravascular stent that is unfolded along the axial direction, the most prominent points on the edge of the radiopaque markers in the fixing hole 304, the fixing hole 305 and the fixing hole 306 are connected sequentially, to form an approximately elliptic envelope 308. The major diameter of the envelope 308 is provided along the axial direction of the intravascular stent 300, and the minor diameter along the circumferential direction of the intravascular stent 300. The major diameter is 1.4097 mm. The minor diameter is 0.3097 mm. The enclosed area of the envelope 308 is 0.4097 mm$^2$. The effective radiopaque area of the radiopaque structure is 0.2919 mm$^2$. The ratio of the effective radiopaque area to the enclosed area of the envelope 110 is 1:1.40.

The effective radiopaque area in this embodiment is almost completely distributed in the axial direction of the intravascular stent 300, which reduces the distribution of the radiopaque marker in the circumferential direction of the stent to a greater extent. When the stent deforms upon being crimped, the wave-shaped rings of the stent are compressed circumferentially. As the proportion of the radiopaque structure in the circumferential dimension of the stent in this embodiment is relatively small, the circumferential compression is allowed for the relatively large scale wave-shaped rings. Therefore, the radiopaque structure enables the intravascular stent 300 to have a relatively small crimped diameter. The crimped diameter of the intravascular stent 300 of this embodiment is about 1.01 mm. For an intravascular stent that has substantially the same structure and material, in the case of not being provided with the radiopaque structure of this embodiment, the crimped diameter is 1.00 mm. Based on comparison tests, the crimped diameter of the intravascular stent provided with the radiopaque structure in this embodiment does not significantly change.

FIG. 3 is a DSA image view of the intravascular stent provided for this embodiment. The first stent on the right is the intravascular stent 300, with the radiopaque structures being disposed at the upper and lower ends of the stent. It can be seen from FIG. 3 that the radiopaque structures have a desirable visibility.

In the other embodiments of the present disclosure, the included angle between the major diameter of the envelope and the axial direction of the framework is less than 45 degrees, or the included angle between the major diameter of the envelope and the axial direction of the framework is less than that between the major diameter and the circumferential direction of the framework. The structure of the framework may be another regular wave-shaped ring, for example, comprising several Z-shaped waves having the same shape and size; or may be another irregular wave-shaped ring, for example, having different sizes and shapes in the proximal-to-distal direction. Briefly, the framework has any structure on the premise of having openings.

The above embodiments should not be construed as limitations of the present disclosure, but merely as exemplifications of preferred embodiments thereof.

It will be appreciated that various changes and modifications may be made to the disclosure as described herein without departing from the concept and scope thereof. Hence, the protection scope of the present disclosure should be based on the claims.

The invention claimed is:

1. An intravascular stent, comprising a framework having openings and at least one radiopaque structure, wherein each of said at least one radiopaque structures comprises fixed bodies and radiopaque markers filled in said fixed bodies, with said fixed bodies connected with said framework, and said fixed bodies are at least partially disposed in said openings, wherein an envelope enclosed area of all the radiopaque markers in each of said at least one radiopaque structures is less than or equal to 2 mm$^2$, and a sum of effective areas of all the radiopaque markers in each of said at least one radiopaque structures is greater than or equal to 0.15 mm$^2$, and a ratio of said sum of effective areas to said envelope enclosed area is greater than or equal to 1:5.

2. The intravascular stent according to claim 1, wherein said envelope enclosed area is less than or equal to 1.5 mm$^2$.

3. The intravascular stent according to claim 1, wherein said envelope enclosed area is less than or equal to 0.7 mm$^2$.

4. The intravascular stent according to claim 1, wherein said sum of effective areas is greater than or equal to 0.19 mm$^2$.

5. The intravascular stent according to claim 1, wherein said sum of effective areas is greater than or equal to 0.22 mm$^2$.

6. The intravascular stent according to claim 1, wherein a ratio of said sum of effective areas to said envelope enclosed area is greater than or equal to 1:4.

7. The intravascular stent according to claim 1, wherein a ratio of said sum of effective areas to said envelope enclosed area is greater than or equal to 1:3.2.

8. The intravascular stent according to claim 1, wherein said radiopaque markers are a heavy metal or a mixture of heavy metal and polymer, and the heavy metal has a mass fraction, and the mass fraction of heavy metal in said mixture is greater than or equal to 70%.

9. The intravascular stent according to claim 8, wherein said heavy metal is at least one of gold, platinum, osmium, rhenium, tungsten, iridium, rhodium or tantalum, and said polymer is selected from PLLA, PLGA, PAGA, PGLA or PLA.

\* \* \* \* \*